(12) United States Patent
Wong et al.

(10) Patent No.: US 7,577,284 B2
(45) Date of Patent: Aug. 18, 2009

(54) OPTICAL DETECTION OF DENTAL CARIES

(75) Inventors: Victor C. Wong, Rochester, NY (US); Rongguang Liang, Penfield, NY (US); Michael A. Marcus, Honeoye Falls, NY (US); Paul O. McLaughlin, Rochester, NY (US); David L. Patton, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 572 days.

(21) Appl. No.: 11/408,360

(22) Filed: Apr. 21, 2006

(65) Prior Publication Data
US 2007/0248931 A1   Oct. 25, 2007

(51) Int. Cl.
*G06K 9/00* (2006.01)
(52) U.S. Cl. .................. 382/128; 382/132; 382/254; 433/29; 433/215
(58) Field of Classification Search .............. 382/128, 382/132, 254; 433/29, 215; 356/497
See application file for complete search history.

(56) References Cited

U.S. PATENT DOCUMENTS

| | | | |
|---|---|---|---|
| 4,184,175 A | 1/1980 | Mullane, Jr. | |
| 4,479,499 A | 10/1984 | Alfano | |
| 4,515,476 A | 5/1985 | Ingmar | |
| 5,306,144 A | 4/1994 | Hibst et al. | |
| 6,122,103 A | 9/2000 | Perkins et al. | |
| 6,231,338 B1 | 5/2001 | de Josselin de Jong et al. | |
| 7,163,397 B2 * | 1/2007 | Hahn et al. | 433/89 |
| 7,270,543 B2 * | 9/2007 | Stookey et al. | 433/215 |
| 2003/0156788 A1 | 8/2003 | Henning | |
| 2004/0202356 A1 | 10/2004 | Stookey et al. | |
| 2004/0236232 A1 | 11/2004 | Jonusauskas et al. | |
| 2004/0240716 A1 | 12/2004 | de Josselin de Jong et al. | |
| 2005/0003323 A1 * | 1/2005 | Katsuda et al. | 433/29 |

FOREIGN PATENT DOCUMENTS

| | | |
|---|---|---|
| WO | WO 03/094771 | 11/2003 |
| WO | WO2004/104927 | 12/2004 |

OTHER PUBLICATIONS

Fried et al.; Imaging caries lesions and lesion progression with polarization sensitive optical coherence tomography; Journal of Biomedical Optics, vol. 7, No. 4, Oct. 2002, pp. 618-627.
Buchalla et al.; Optimal Camera and Illumincation Angulations for Detection of Interproximal Caries Using Quantitative Light-Induced Fluorescence; Caries Research 2002, pp. 320-326, May 22, 2002.

* cited by examiner

*Primary Examiner*—Vikkram Bali
*Assistant Examiner*—Ali Bayat

(57) ABSTRACT

A method for caries detection uses an image capture device (30, 32) to obtain fluorescence image data from the tooth (20) by illuminating the tooth to excite fluorescent emission. A first enhanced image of the tooth is then obtained by illuminating the tooth at a first incident angle, obtaining a back-scattered reflectance image data from the tooth tissue, and combining the back-scattered reflectance image data with the fluorescence image data. A second enhanced image of the tooth is then obtained by illuminating the tooth at a second incident angle, obtaining a back-scattered reflectance image data from the tooth tissue, and combining the back-scattered reflectance image data with the fluorescence image data. The first and second enhanced images are then analyzed to select and display the best-contrast image. This method provides high contrast images for carious regions (58) on all tooth surfaces.

40 Claims, 16 Drawing Sheets

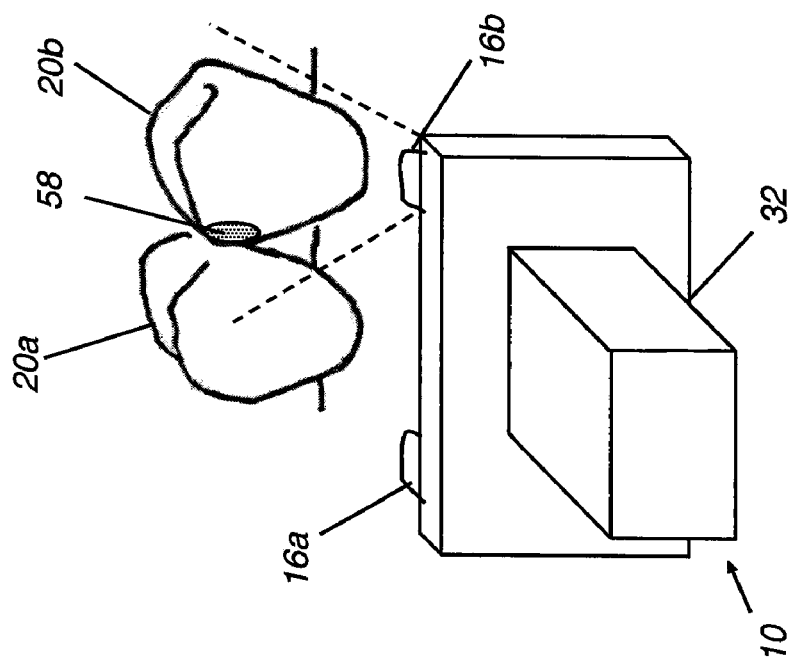
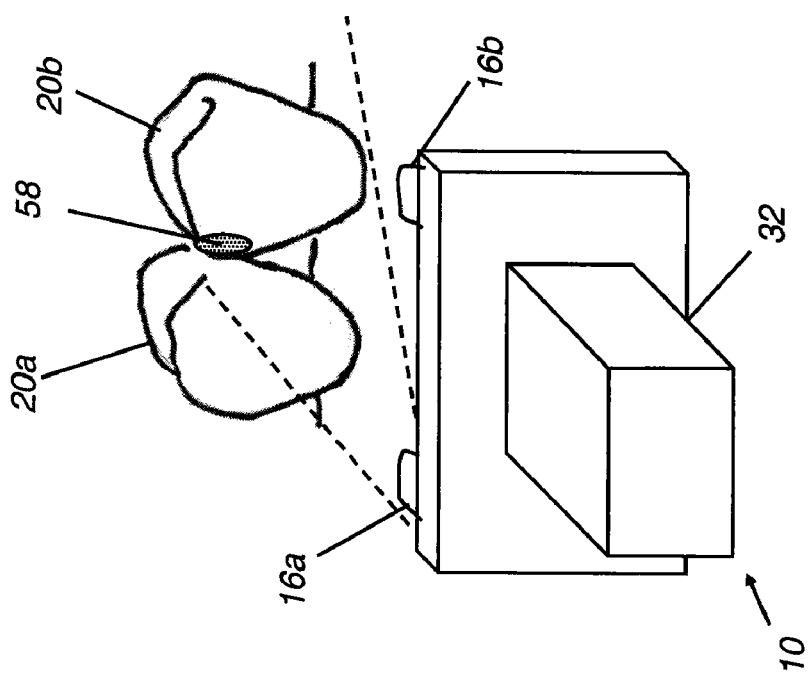

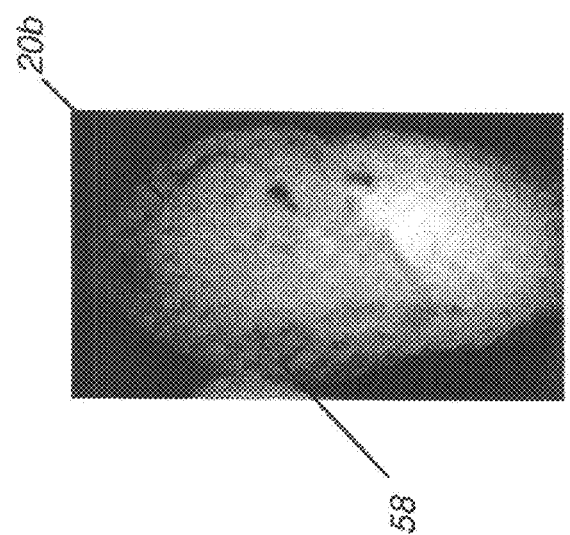
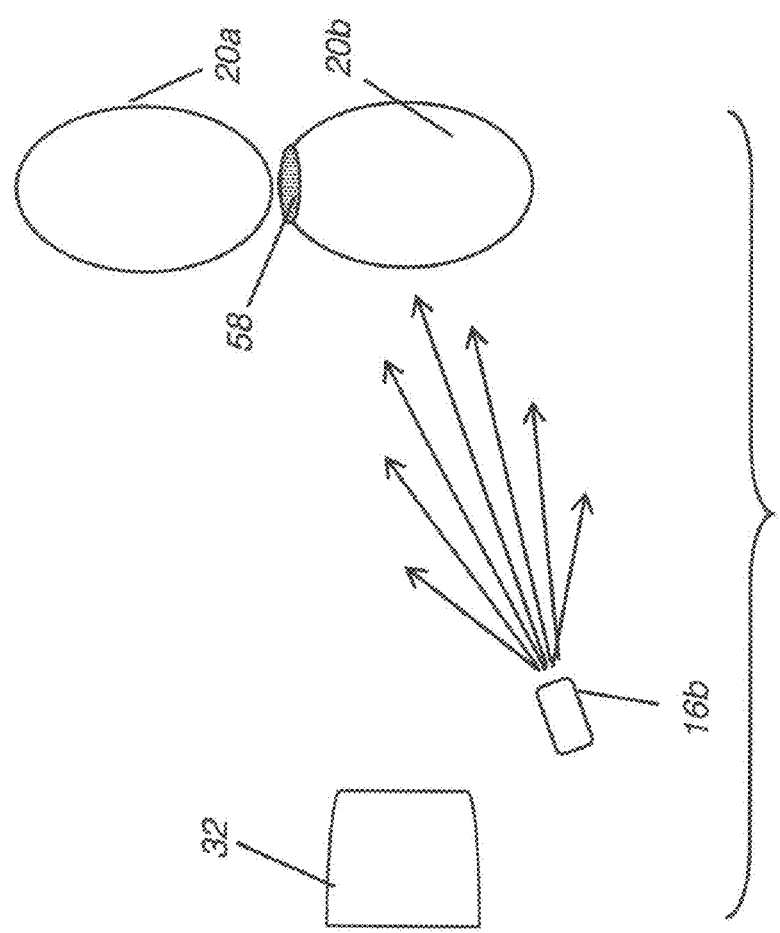
FIG. 11B
FIG. 11A

OPTICAL DETECTION OF DENTAL CARIES

CROSS REFERENCE TO RELATED APPLICATIONS

Reference is made to commonly-assigned copending U.S. application Ser. No. 11/262,869, filed Oct. 31, 2005, entitled METHOD AND APPARATUS FOR DETECTION OF CARIES, by Wong et al., the disclosure of which is incorporated herein.

FIELD OF THE INVENTION

This invention generally relates to methods and apparatus for dental imaging and more particularly relates to an improved method for caries detection on all surfaces, including interproximal surface, using light fluorescence and reflectance.

BACKGROUND OF THE INVENTION

In spite of improvements in detection, treatment, and prevention techniques, dental caries remains a widely prevalent condition affecting people of all age groups. If not properly and promptly treated, caries can lead to permanent tooth damage and even to loss of teeth.

Traditional methods for caries detection include visual examination and tactile probing with a sharp dental explorer device, often assisted by radiographic (x-ray) imaging. Detection using these methods can be somewhat subjective, varying in accuracy due to many factors, including practitioner expertise, location of the infected site, extent of infection, viewing conditions, accuracy of x-ray equipment and processing, and other factors. There are also hazards associated with conventional detection techniques, including the risk of damaging weakened teeth and spreading infection with tactile methods as well as exposure to x-ray radiation. By the time caries is evident under visual and tactile examination, the disease is generally in an advanced stage, requiring a filling and, if not timely treated, possibly leading to tooth loss.

In response to the need for improved caries detection methods, there has been considerable interest in improved imaging techniques that do not employ x-rays. One method that has been commercialized employs fluorescence, caused when teeth are illuminated with high intensity blue light. This technique, termed quantitative light-induced fluorescence (QLF), operates on the principle that sound, healthy tooth enamel yields a higher intensity of fluorescence under excitation from some wavelengths than does de-mineralized enamel that has been damaged by caries infection. The strong correlation between mineral loss and loss of fluorescence for blue light excitation is then used to identify and assess carious areas of the tooth. A different relationship has been found for red light excitation, a region of the spectrum for which bacteria and bacterial by-products in carious regions absorb and fluoresce more pronouncedly than do healthy areas.

Among proposed solutions for optical detection of caries are the following:

U.S. Pat. No. 4,515,476 (Ingmar) discloses use of a laser for providing excitation energy that generates fluorescence at some other wavelength for locating carious areas.

U.S. Pat. No. 6,231,338 (de Josselin de Jong et al.) discloses an imaging apparatus for identifying dental caries using fluorescence detection.

U.S. Patent Application Publication No. 2004/0240716 (de Josselin de Jong et al.) discloses methods for improved image analysis for images obtained from fluorescing tissue.

U.S. Pat. No. 4,479,499 (Alfano) describes a method for using transillumination to detect caries based on the translucent properties of tooth structure.

Among commercialized products for dental imaging using fluorescence behavior is the QLF Clinical System from Inspektor Research Systems BV, Amsterdam, The Netherlands. Using a different approach, the Diagnodent Laser Caries Detection Aid from KaVo Dental Corporation, Lake Zurich, Ill., detects caries activity monitoring the intensity of fluorescence of bacterial by-products under illumination from red light.

U.S. Patent Application Publication No. 2004/0202356 (Stookey et al.) describes mathematical processing of spectral changes in fluorescence in order to detect caries in different stages with improved accuracy. Acknowledging the difficulty of early detection when using spectral fluorescence measurements, the '2356 Stookey et al. disclosure describes approaches for enhancing the spectral values obtained, effecting a transformation of the spectral data that is adapted to the spectral response of the camera that obtains the fluorescent image.

While the disclosed methods and apparatus show promise in providing non-invasive, non-ionizing imaging methods for caries detection, there is still room for improvement. One recognized drawback with existing techniques that employ fluorescence imaging relates to image contrast. The image provided by fluorescence generation techniques such as QLF can be difficult to assess due to relatively poor contrast between healthy and infected areas. As noted in the '2356 Stookey et al. disclosure, spectral and intensity changes for incipient caries can be very slight, making it difficult to differentiate non-diseased tooth surface irregularities from incipient caries.

Overall, it is well-recognized that, with fluorescence techniques, the image contrast that is obtained corresponds to the severity of the condition. Accurate identification of caries using these techniques often requires that the condition be at a more advanced stage, beyond incipient or early caries, because the difference in fluorescence between carious and sound tooth structure is very small for caries at an early stage. In such cases, detection accuracy using fluorescence techniques may not show marked improvement over conventional methods. Because of this shortcoming, the use of fluorescence effects appears to have some practical limits that prevent accurate diagnosis of incipient caries. As a result, a caries condition may continue undetected until it is more serious, requiring a filling, for example.

Detection of caries at very early stages is of particular interest for preventive dentistry. As noted earlier, conventional techniques generally fail to detect caries at a stage at which the condition can be reversed. As a general rule of thumb, incipient caries is a lesion that has not penetrated substantially into the tooth enamel. Where such a caries lesion is identified before it threatens the dentin portion of the tooth, remineralization can often be accomplished, reversing the early damage and preventing the need for a filling. More advanced caries, however, grows increasingly more difficult to treat, most often requiring some type of filling or other type of intervention.

In order to take advantage of opportunities for non-invasive dental techniques to forestall caries, it is necessary that caries be detected at the onset. In many cases, as is acknowledged in the '2356 Stookey et al. disclosure, this level of detection has been found to be difficult to achieve using existing fluorescence imaging techniques, such as QLF. As a result, early caries can continue undetected, so that by the time positive detection is obtained, the opportunity for reversal using low-cost preventive measures can be lost.

One particular area of difficulty for caries detection relates to interproximal caries, that is, caries occurring on surfaces along the gap between adjacent teeth. In comparison with other portions of the tooth surface, such as with buccal or lingual portions, interproximal areas can be considerably more difficult to illuminate and to view. For viewing interproximal tooth tissue using conventional fluorescence imaging, it has been demonstrated that the excitation illumination that causes the fluorescence can be directed to the tooth from any of a range of angles within the same plane, that is, the plane containing the normals to the buccal, occlusal, and lingual surfaces, with little or no perceptible improvement between illumination at one angular orientation and another. This conclusion is reached, for example, in a paper by Buchalla, Lennon, van der Veen, and Stookey, entitled "Optimal Camera and Illumination Angulations for Detection of Interproximal Caries Using Quantitative Light-Induced Fluorescence" in Caries Research 2002, pp. 320-326. This paper suggests the importance of camera angle, but dismisses the impact of varying illumination angle for obtaining a suitable fluorescence image. Variation of illumination angle for outside the plane containing the normals to the buccal, occlusal, and lingual surfaces is not considered. Neither is the variation of illumination angle for non-fluorescence optical signal, such as reflectance, considered.

Interproximal caries is a highly prevalent form of dental caries that can be difficult to detect. Although imaging solutions such as those using fluorescence generation have shown some utility for detection of caries over areas of the tooth that can be more easily viewed, these solutions have shown little success in detecting interproximal caries. Thus, it can be seen that there is a need for a non-invasive, non-ionizing imaging method for caries detection that offers improved accuracy for detection of caries in its earlier stages and of interproximal caries.

SUMMARY OF THE INVENTION

The present invention provides a method for caries detection comprising:
(a) disposing an image capture device at a position facing a tooth;
(b) obtaining fluorescence image data from the tooth by illuminating the tooth to excite fluorescent emission and obtaining a fluorescence image from the emitted light;
(c) obtaining a first enhanced image of the tooth by:
  (i) illuminating the tooth at a first incident angle;
  (ii) obtaining, from back-scattered light, back-scattered reflectance image data from the tooth tissue; and
  (iii) combining the back-scattered reflectance image data with the fluorescence image data to form the first enhanced image;
(d) obtaining a second enhanced image of the tooth by:
  (i) illuminating the tooth at a second incident angle, different from the first incident angle;
  (ii) obtaining, from back-scattered light, back-scattered reflectance image data from the tooth tissue; and
  (iii) combining the back-scattered reflectance image data with the fluorescence image data to form the second enhanced image;
(e) analyzing the first and second enhanced images to select a best-contrast image; and
(f) displaying the best-contrast image.

It is a feature of the present invention that it combines both fluorescence and reflectance image data for improved dental imaging.

It is an advantage of the present invention that it offers enhancement over existing fluorescence imaging techniques, useful for detection of caries on all surfaces, including interproximal caries.

It is a further advantage of the present invention that it provides an imaging method for detection of interproximal caries with improved contrast over existing methods.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the detailed description of the invention presented below, reference is made to the accompanying drawings, in which:

FIGS. 8A and 8B are perspective views showing a camera obtaining an image of an interproximal area at two different illumination angles, according to the method of the present invention;

FIGS. 11A and 11B illustrate angled illumination from one side of the camera and the resulting FIRE image;

DETAILED DESCRIPTION OF THE INVENTION

Figure 1:
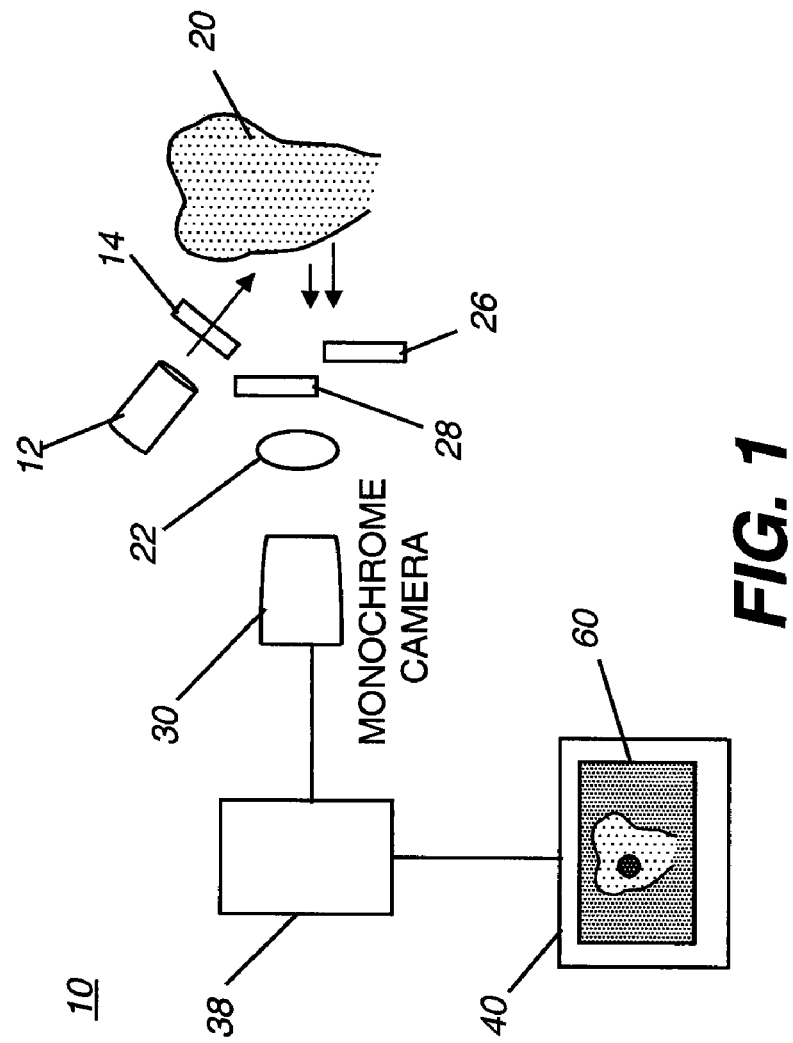
FIG. 1 is a schematic block diagram of an imaging apparatus for caries detection according to one embodiment.

The present description is directed in particular to elements forming part of, or cooperating more directly with, apparatus in accordance with the invention. It is to be understood that elements not specifically shown or described may take various forms well known to those skilled in the art.

As noted in the preceding background section, it is known that fluorescence can be used to detect dental caries using either of two characteristic responses: First, excitation by a blue light source causes healthy tooth tissue to fluoresce in the green spectrum. Secondly, excitation by a red light source can cause bacterial by-products, such as those indicating caries, to fluoresce in the red spectrum.

In order for an understanding of how light is used in the present invention, it is important to give more precise definition to the terms "reflectance" and "back-scattering" as they are used in biomedical applications in general and, more particularly, in the method and apparatus of the present invention. In broadest optical parlance, reflectance generally denotes the sum total of both specular reflectance and scattered reflectance. (Specular reflection is that component of the excitation light that is reflected by the tooth surface at the same angle as the incident angle.) In many biomedical applications, however, as in the dental application of the present invention, the specular component of reflectance is of no interest and is, instead, generally detrimental to obtaining an image or measurement from a sample. The component of reflectance that is of interest for the present application is from back-scattered light only. Specular reflectance must be blocked or otherwise removed from the imaging path. With this distinction in mind, the term "back-scattered reflectance" is used in the present application to denote the component of reflectance that is of interest. "Back-scattered reflectance" is defined as that component of the excitation light that is elastically back-scattered over a wide range of angles by the illuminated tooth structure. "Reflectance image" data, as this term is used in the present invention, refers to image data obtained from back-scattered reflectance only, since specular reflectance is blocked or kept to a minimum. In the scientific literature, back-scattered reflectance may also be referred to as back-reflectance or simply as backscattering. Back-scattered reflectance is at the same wavelength as the excitation light.

It has been shown that light scattering properties differ between sound and carious dental regions. In particular, reflectance of light from the illuminated area can be at measurably different levels for normal versus carious areas. This change in reflectance, taken alone, may not be sufficiently pronounced to be of diagnostic value when considered by itself, since this effect is very slight, although detectable. For more advanced stages of caries, for example, back-scattered reflectance may be less effective an indicator than at earlier stages.

The inventors have found, however, that this back-scattered reflectance change can be used in conjunction with the fluorescent effects to more clearly and more accurately pinpoint a carious location. Moreover, the inventors have observed that the change in light scattering activity, while it can generally be detected wherever a caries condition exists, is more pronounced in areas of incipient caries. This back-scattered reflectance change is evident at early stages of caries, even when fluorescent effects are least pronounced.

The present invention takes advantage of the observed back-scattering behavior for incipient caries and uses this effect, in combination with fluorescence effects described previously in the background section, to provide an improved capability for dental imaging to detect caries. The inventive technique, hereafter referred to as fluorescence imaging with reflectance enhancement (FIRE), not only helps to increase the contrast of images over that of earlier approaches, but also makes it possible to detect incipient caries at stages where preventive measures are likely to effect remineralization, repairing damage done by the caries infection at a stage well before more complex restorative measures are necessary. Advantageously, FIRE detection can be accurate at an earlier stage of caries infection than has been exhibited using existing fluorescence approaches that measure fluorescence alone. Additionally, when suitable illumination apparatus and techniques are employed, the FIRE detection methods can be used to obtain more effective detection of interproximal caries than has been previously available.

It is emphasized that while reflectance has been used to distinguish carious lesions from sound tooth structure, such as in U.S. Pat. No. 4,184,175 (Mullane, Jr.), U.S. Patent Application Publication No. 2003/0156788 (Henning), and PCT Application No. WO 2003/094771 (Karazivan et al.), it has always been used as stand-alone data; it has not been recognized that the additional information in the reflectance signal can be combined with fluorescence to provide a higher contrast image for detection of dental caries. And in conventional fluorescence measurements such as those obtained using QLF techniques, reflectance itself is an effect that is avoided rather than utilized. A filter is usually employed to block off all excitation light from reaching the camera or other detection device. The FIRE method in the present invention, by combining both the fluorescence and reflectance images through image processing, provides improved caries detection capabilities over prior art methods using either fluorescence or reflectance alone or separately.

Imaging Apparatus

Referring to FIG. 1, there is shown an imaging apparatus 10 for caries detection using the FIRE method in one embodiment. A light source 12 directs an incident light, at a blue wavelength range or other suitable wavelength range, toward tooth 20 through an optional lens 14 or other light beam conditioning component. Two components of light are then detected by a monochrome camera 30 through a lens 22: a back-scattered light component having the same wavelength as the incident light and having measurable reflectance; and a fluorescent light that has been excited due to the incident light. For FIRE imaging, specular reflection causes false positives and is undesirable.

In the embodiment of FIG. 1, monochrome camera 30 has color filters 26 and 28. One of color filters 26 and 28 is used during reflectance imaging, the other is used during fluorescence imaging. A processing apparatus 38 obtains and processes the reflectance and fluorescence image data and forms a FIRE image 60. FIRE image 60 is an enhanced diagnostic image that can be printed or can appear on a display 40. FIRE image 60 data can also be transmitted to storage or transmitted to another site for display.

Figure 2:
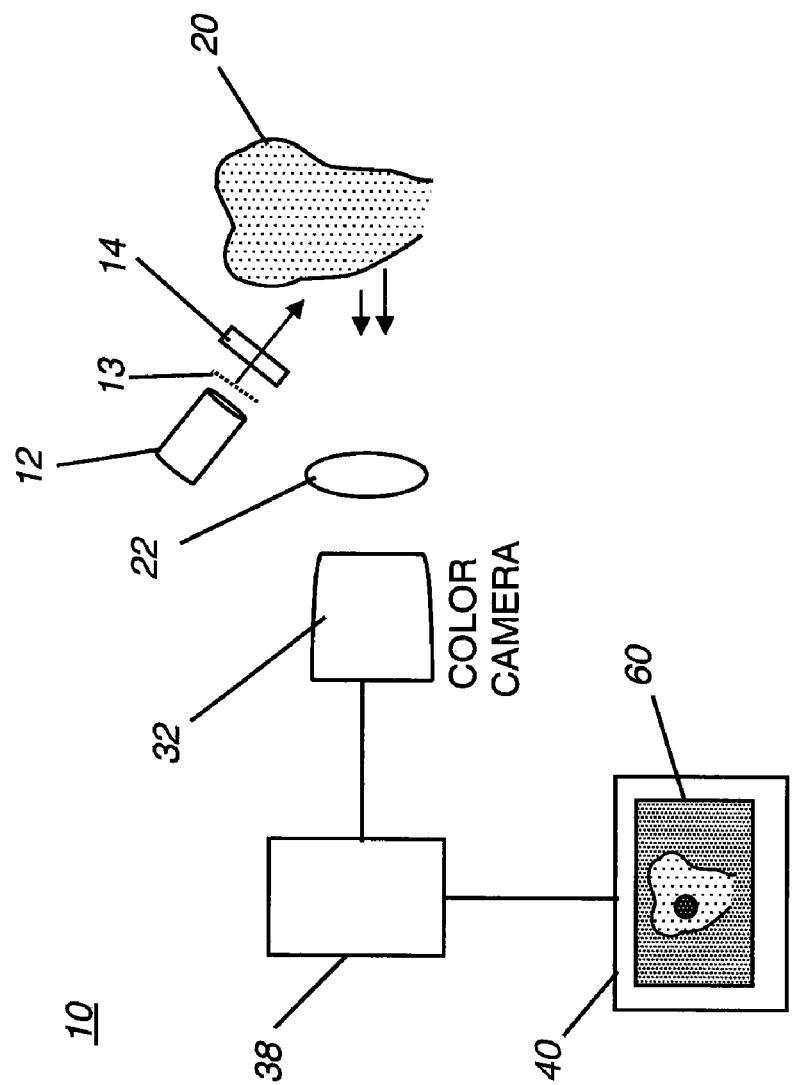
FIG. 2 is a schematic block diagram of an imaging apparatus for caries detection according to an alternate embodiment.

Referring to FIG. 2, there is shown an alternate embodiment using a color camera 32. With this arrangement, auxiliary filters would not generally be needed, since color camera 32 would be able to obtain the reflectance and fluorescence images from the color separations of the full color image of tooth 20.

Light source 12 is typically centered around a blue wavelength, such as about 405 nm in one embodiment. In practice, light source 12 could emit light ranging in wavelength from an upper ultraviolet range to a deeper blue, between about 300 and 500 nm. Light source 12 can be a laser or could be fabricated using one or more light emitting diodes (LEDs). Alternately, a broadband source, such as a xenon lamp, having a supporting color filter for passing the desired wavelengths could be used. Lens 14 or other optical element may serve to condition the incident light, such as by controlling the uniformity and size of the illumination area. For example, a diffuser 13, shown as a dotted line in FIG. 2, might be used before or after lens 14 to smooth out the hot spots of an LED beam. The path of illumination light might include light guiding or light distributing structures such as an optical fiber or a liquid light guide, for example (not shown). Light level is typically a few milliwatts in intensity, but can be more or less, depending on the light conditioning and sensing components used.

Figure 3:
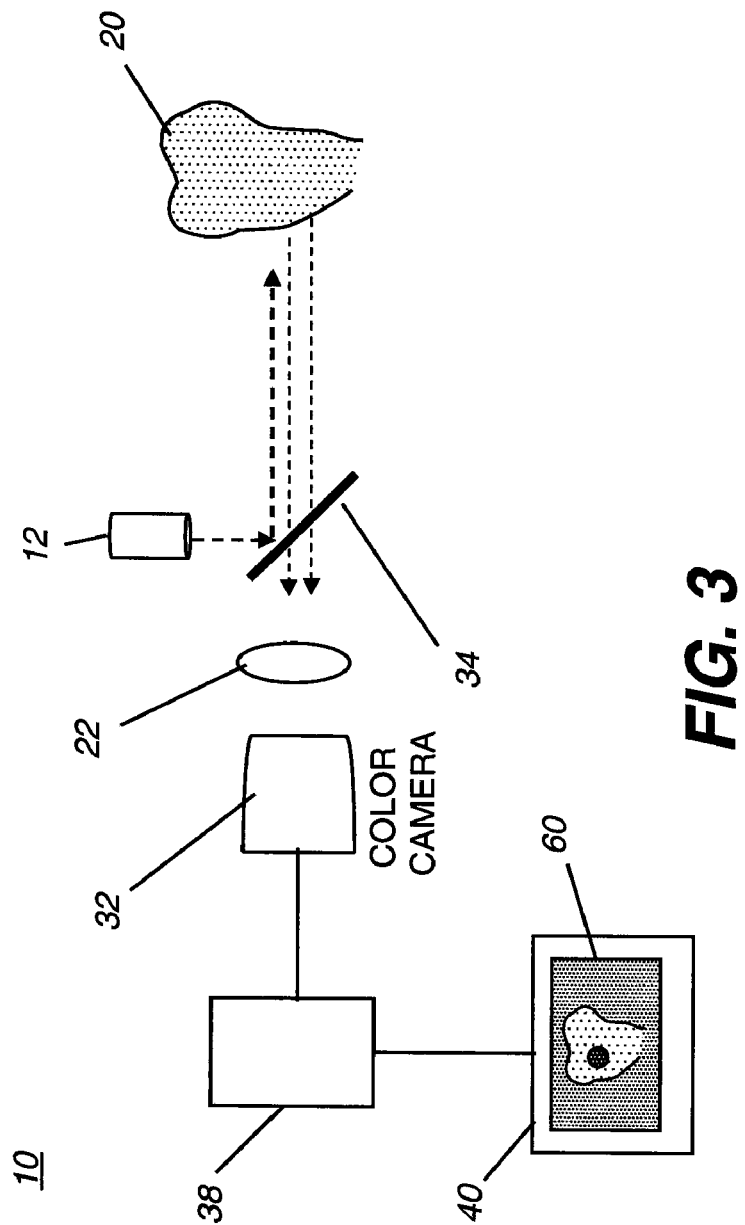
FIG. 3 is a schematic block diagram of an imaging apparatus for caries detection according to an alternate embodiment using a beamsplitter.

Referring to FIG. 3, the illumination arrangement could alternately direct light at normal incidence, turned through a beamsplitter 34. Color camera 32 would then be disposed to obtain the image light that is transmitted through beamsplitter 34. Other options for illumination include multiple light sources directed at the tooth with angular incidence from one or more sides. Alternately, the illumination might use an annular ring or an arrangement of LED sources distributed about a center such as in a circular array to provide light uniformly from multiple angles. Illumination could also be provided through an optical fiber or fiber array. The illumination arrangement best suited for interproximal caries detection is described subsequently.

The imaging optics, represented as lens 22 in FIGS. 1-3, could include any suitable arrangement of optical components, with possible configurations ranging from a single lens component to a multi-element lens. Clear imaging of the tooth surface, which is not flat but can have areas that are both smoothly contoured and highly ridged, requires that imaging optics have sufficient depth of focus. Preferably, for optimal resolution, the imaging optics provide an image size that substantially fills the sensor element of the camera. Telecentric optics are advantaged for lens 22, providing image-bearing light that is not highly dependent on ray angle.

Image capture can be performed by either monochrome camera 30 (FIG. 1) or color camera 32 (FIG. 2). Typically, camera 30 or 32 employs a CMOS or CCD sensor, and is handheld. The monochrome version would typically employ a retractable spectral filter 26, 28 suitable for the wavelength of interest. For light source 12 having a blue wavelength, spectral filter 26 for capturing reflectance image data would transmit predominately blue light. Spectral filter 28 for capturing fluorescence image data would transmit light at a different wavelength, such as predominately green light. Preferably, spectral filters 26 and 28 are automatically switched into place to allow capture of both reflectance and fluorescence images in very close succession. Both images are obtained from the same position to allow accurate registration of the image data.

Spectral filter 28 would be optimized with a pass-band that captures fluorescence data over a range of suitable wavelengths. The fluorescent effect that has been obtained from tooth 20 can have a relative broad spectral distribution in the visible range, with light emitted that is outside the wavelength range of the light used for excitation. The fluorescent emission is typically between about 450 nm and 600 nm, while generally peaking in the green region, roughly from around 510 nm to about 550 nm. Thus a green light filter is generally preferred for spectral filter 28 in order to obtain this fluorescence image at its highest energy levels. With color camera 32, the green image data is generally used for this same reason. This green image data is also obtained through a green light filter, such as a green filter in a color filter array (CFA), as is well known to those skilled in the color image capture art. However, other ranges of the visible spectrum could also be used in other embodiments.

Camera controls are suitably adjusted for obtaining each type of image. For example, when capturing the fluorescence image, it is necessary to make appropriate exposure adjustments for gain, shutter speed, and aperture, since this image may not be intense. When using color camera 32 (FIG. 2), color filtering is performed by the color filter arrays on the camera image sensor. The reflectance image is captured in the blue color plane; simultaneously, the fluorescence image is captured in the green color plane. That is, a single exposure captures both back-scattered reflectance and fluorescence images.

Processing apparatus 38 is typically a computer workstation but may, in its broadest application, be any type of control logic processing component or system that is capable of obtaining image data from camera 30 or 32 and executing image processing algorithms upon that data to generate the FIRE image 60 data. Processing apparatus 38 may be local or may connect to image sensing components over a networked interface.

Figure 5:
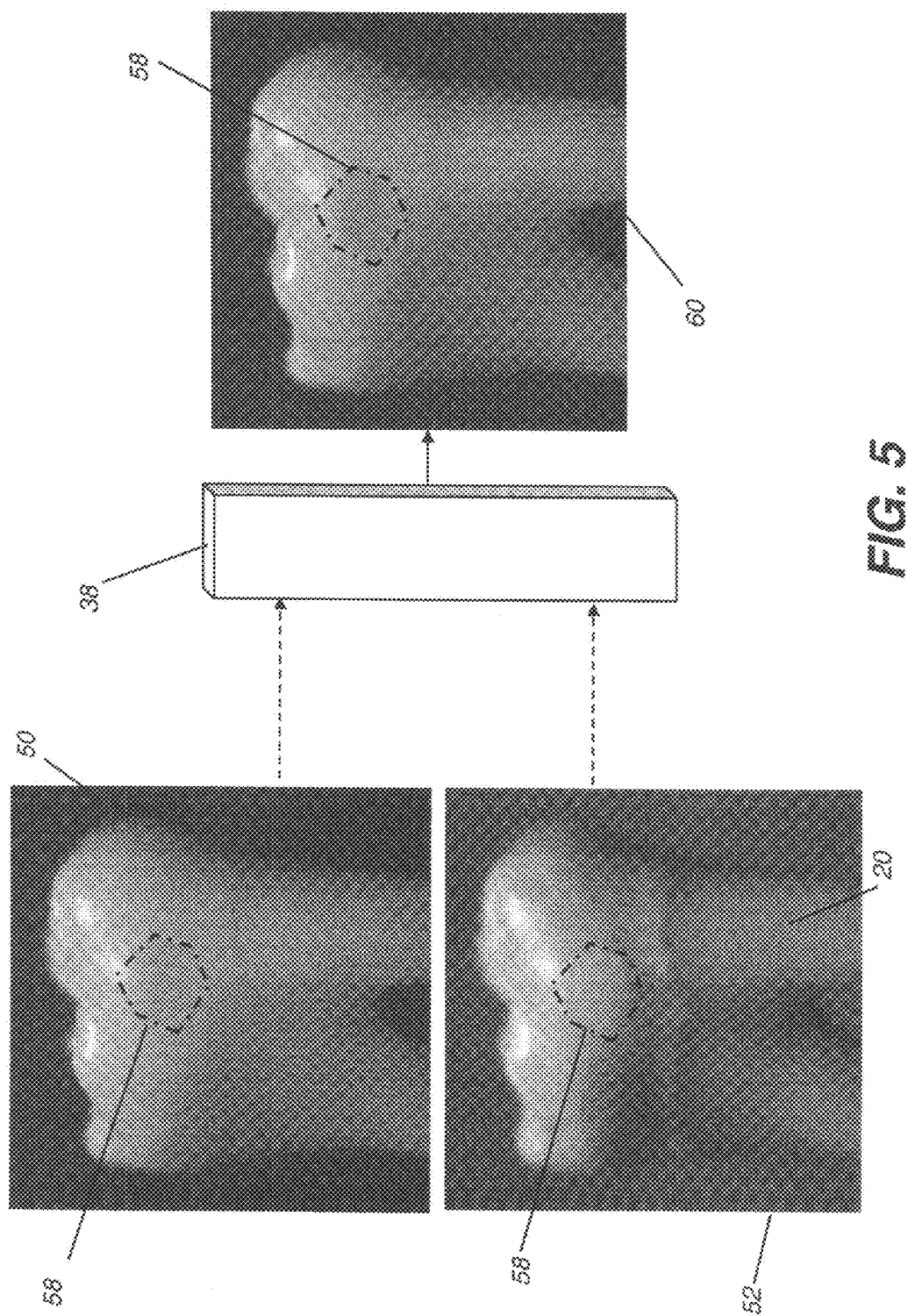
FIG. 5 is a view showing the process for combining dental image data to generate a fluorescence image with reflectance enhancement according to the present invention.

Referring to FIG. 5, there is shown, in schematic form, how the FIRE image 60 is formed according to the present invention. Two images of tooth 20 are obtained, a green fluorescence image 50 and a blue reflectance image 52. As noted earlier, it must be emphasized that the reflectance light used for reflectance image 52 and its data is from back-scattered reflectance, with specular reflectance blocked or kept as low as possible. In the example of FIG. 5, there is a carious region 58, represented in phantom outline in each of images 50, 52, and 60 that causes a slight decrease in fluorescence and a slight increase in reflectance. The carious region 58 may be imperceptible or barely perceptible in either fluorescence image 50 or reflectance image 52, taken individually. Processing apparatus 38 operates upon the image data using an image processing algorithm as discussed below for both images 50 and 52 and provides FIRE image 60 as a result. The contrast between carious region 58 and sound tooth structure is heightened, so that a caries condition is made more visible in FIRE image 60.

Figure 6:
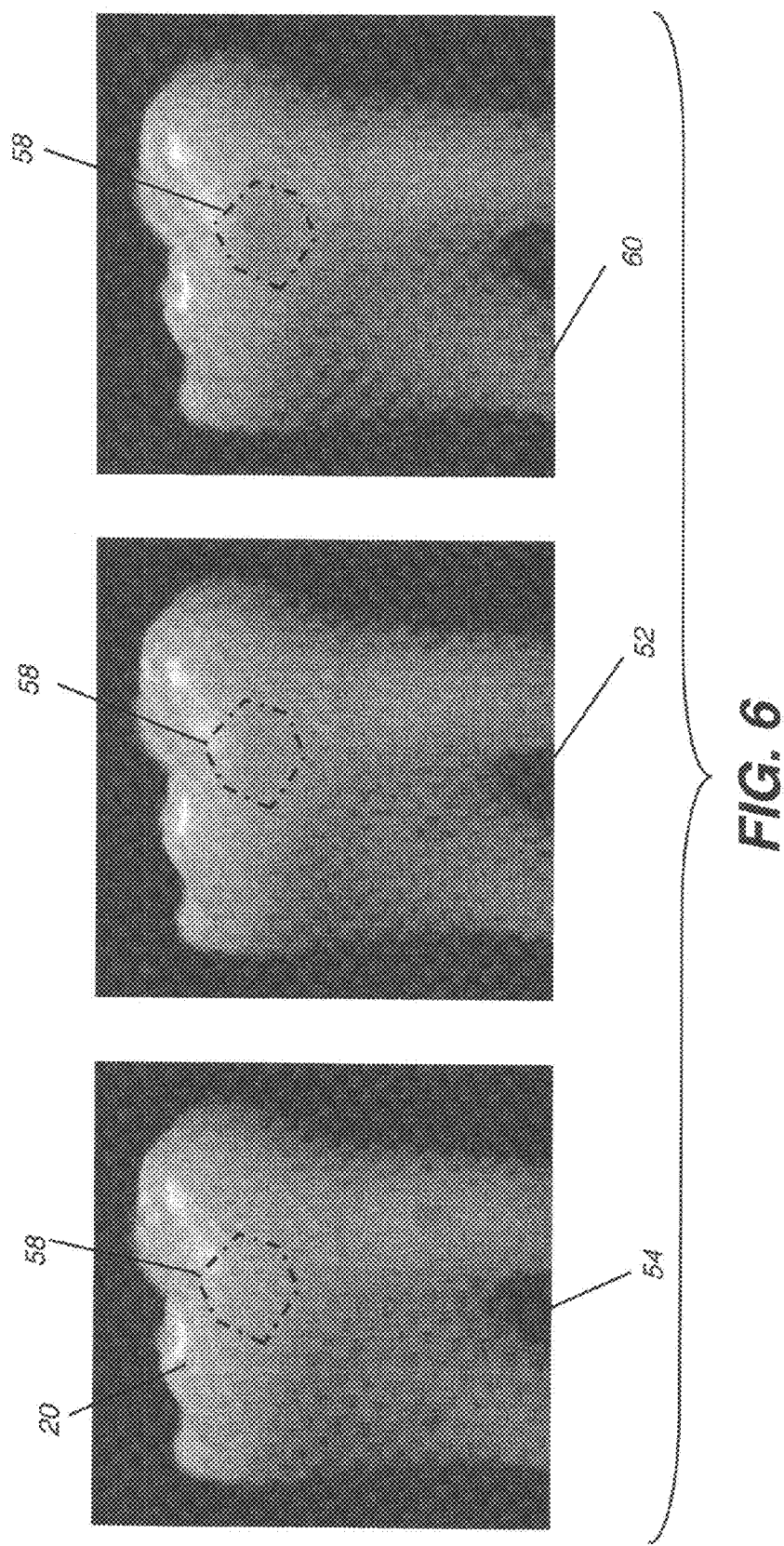
FIG. 6 is a composite view showing the contrast improvement of the present invention in a side-by-side comparison with conventional visual and fluorescence methods.

FIG. 6 shows the contrast improvement of the present invention in a side-by-side comparison with a visual white-light image 54 and conventional fluorescence methods. For caries at a very early stage, the carious region 58 may look indistinct from the surrounding healthy tooth structure in white-light image 54, either as perceived directly by eye or as captured by an intraoral camera. In the green fluorescence image 52 captured by existing fluorescence method, the carious region 58 may show up as a very faint, hardly noticeable shadow. In contrast, in the FIRE image 60 generated by the present invention, the same carious region 58 shows up as a darker, more detectable spot. Clearly, the FIRE image 60, with its contrast enhancement, offers greater diagnostic value.

Image Processing

As described earlier with reference to FIGS. 5 and 6, processing of the image data uses both the reflectance and fluorescence image data to generate a final image that can be used to identify carious areas of the tooth. There are a number of alternative processing methods for combining the reflectance and fluorescence image data to form FIRE image 60 for diagnosis. In one embodiment, this image processing performs the following operation for each pixel:

$$(m*F_{value})-(n*R_{value}) \quad (1)$$

where m and n are suitable multipliers (positive coefficients) and $F_{value}$ and $R_{value}$ are the code values obtained from fluorescence and reflectance image data, respectively.

Back-scattered reflectance is higher (brighter) for image pixels in the carious region, yielding a higher reflectance value $R_{value}$ for these pixels than for surrounding pixels. The fluorescence, meanwhile, is lower (darker) for image pixels in the carious region, yielding a lower fluorescence value $F_{value}$ for these pixels than for surrounding pixels. For a pixel in a carious region, the fluorescence is considerably weaker in intensity compared to the reflectance. After multiplying the fluorescence and reflectance by appropriate scalar multipliers m and n, respectively, where m>n, the scaled fluorescence values of all pixels are made to exceed or equal to the corresponding scaled reflectance values:

$$(m*F_{value}) > \text{or} = (n*R_{value}). \quad (2)$$

Subtraction of the scaled back-scattered reflectance value from the scaled fluorescence value for each pixel then results in a processed image where the contrast between the intensity values for pixels in the carious region and pixels in sound region is accentuated, resulting in a contrast enhancement that can be readily displayed and recognized. In one embodiment, scalar multiplier n for reflectance value $R_{value}$ is one.

Figure 7:
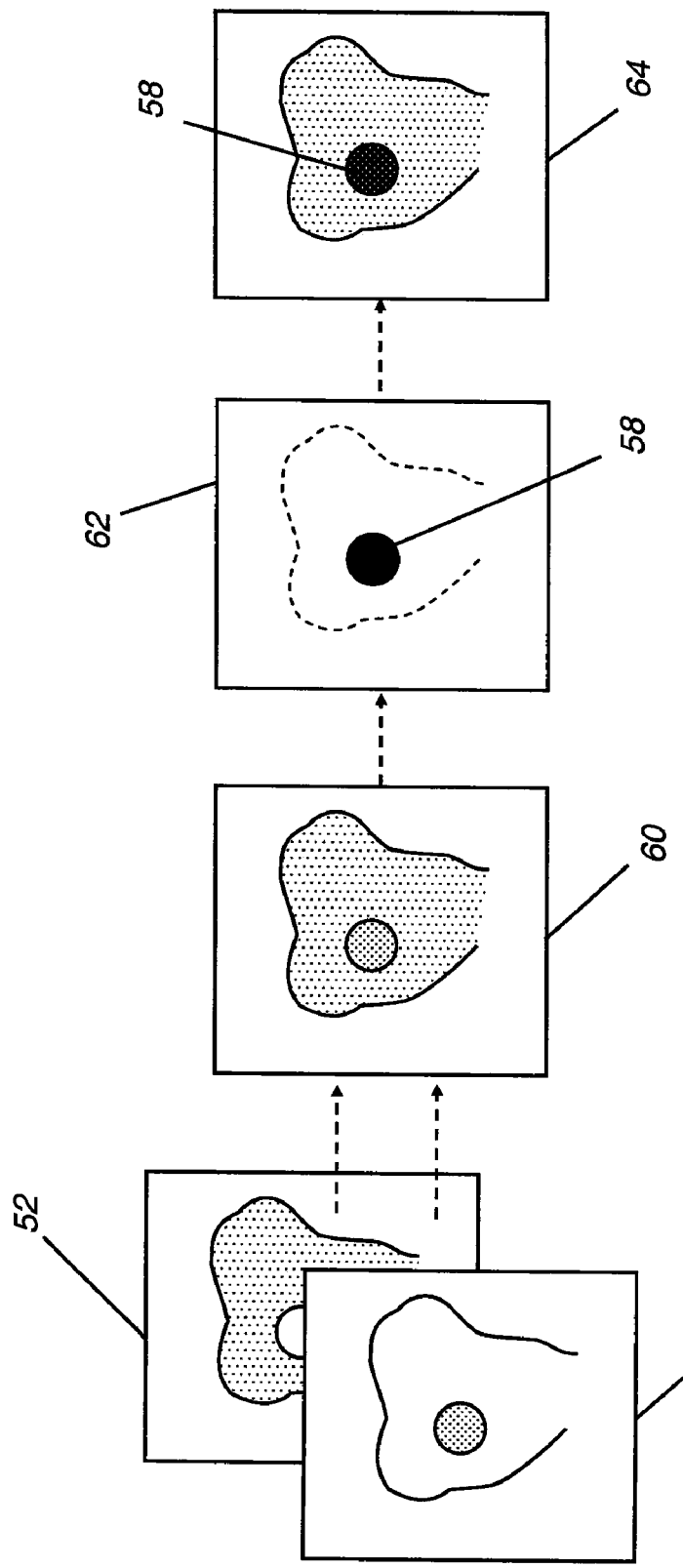
FIG. 7 is a block diagram showing a sequence of image processing for generating an enhanced threshold image according to one embodiment.

Following an initial combination of fluorescence and reflectance values as given earlier with reference to the example of expression (1), additional image processing may also be of benefit. A thresholding operation, executed using image processing techniques familiar to those skilled in the imaging arts, or some other suitable conditioning of the combined image data used for FIRE image 60, may be used to further enhance the contrast between a carious region and sound tooth structure. Referring to FIG. 7, there is shown, in block diagram form, a sequence of image processing for generating an enhanced threshold FIRE image 64 according to one embodiment. Fluorescence image 50 and reflectance image 52 are first combined to form FIRE image 60, as described previously. A thresholding operation is next performed, providing threshold image 62 that defines more clearly the area of interest, carious region 58. Then, threshold image 62 is combined with original FIRE image 60 to generate enhanced threshold FIRE image 64. Similarly, the results of threshold detection can also be superimposed onto a white light image 54 (FIG. 6) in order to definitively outline the location of a carious infection.

The choice of appropriate coefficients m and n is dependent on the spectral content of the light source and the spectral response of the image capture system. There is variability in the center wavelength and spectral bandwidth from one LED to the next, for example. Similarly, variability exits in the spectral responses of the color filters and image sensors of different image capture systems. Such variations affect the relative magnitudes of the measured reflectance and fluorescence values. Therefore, it may be necessary to determine a different m and n value for each imaging apparatus 10 as a part of an initial calibration process. A calibration procedure used during the manufacturing of imaging apparatus 10 can then optimize the m and n values to provide the best possible contrast enhancement in the FIRE image that is formed.

In one calibration sequence, a spectral measurement of the light source 12 used for reflectance imaging is obtained. Then, spectral measurement is made of the fluorescent emission that is excited from the tooth. This data provides a profile of the relative amount of light energy available over each wavelength range of interest. Then the spectral response of camera 30 (with appropriate filters) or 32 is quantified against a known reference. These data are then used, for example, to generate a set of optimized multiplier m and n values to be used by processing apparatus 38 of the particular imaging apparatus 10 for forming FIRE image 60.

It can be readily appreciated that any number of more complex image processing algorithms could alternately be used for combining the reflectance and fluorescence image data in order to obtain an enhanced image that identifies carious regions more clearly. It may be advantageous to apply a number of different imaging algorithms to the image data in order to obtain the most useful result. In one embodiment, an operator can elect to use any of a set of different image processing algorithms for conditioning the fluorescence and reflectance image data obtained. This would allow the operator to check the image data when processed in a number of different ways and may be helpful for optimizing the detection of carious lesions having different shape-related characteristics or that occur over different areas of the tooth surface.

It is emphasized that the image contrast enhancement achieved in the present invention, because it employs both reflectance and fluorescence data, is advantaged over conventional methods that use fluorescent image data only. Conventionally, where only fluorescence data is obtained, image processing has been employed to optimize the data, such as to transform fluorescence data based on spectral response of the camera or of camera filters or other suitable characteristics. For example, the method of the '2356 Stookey et al. disclosure, cited above, performs this type of optimization, transforming fluorescence image data based on camera response. However, these conventional approaches overlook the added advantage of additional image information that the back-scattered reflectance data obtains.

Alternate Embodiments

The method of the present invention admits a number of alternate embodiments. For example, the contrast of either or both of the reflectance and fluorescence images may be improved by the use of a polarizing element. It has been observed that enamel, having a highly structured composition, is sensitive to the polarization of incident light. Polarized light has been used to improve the sensitivity of dental imaging techniques, for example, in the article by Fried et al., "Imaging Caries Lesions and Lesion Progression with Polarization Sensitive Optical Coherence Tomography" in Journal of Biomedical Optics, Vol. 7 No. 4, October 2002, pp. 618-627.

Specular reflection tends to preserve the polarization state of the incident light. For example, where the incident light is S-polarized, the specular reflected light is also S-polarized. Back-scattering, on the other hand, tends to de-polarize or randomize the polarization of the incident light. Where incident light is S-polarized, back-scattered light has both S- and P-polarization components. Using a polarizer and analyzer, this difference in polarization handling can be employed to help eliminate unwanted specular reflectance from the reflectance image, so that only back-scattered reflectance is obtained.

Figure 4B:
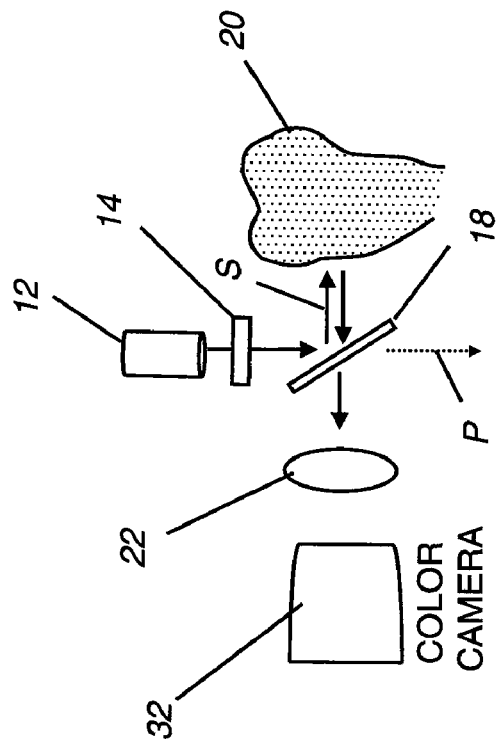
FIG. 4B is a schematic block diagram of an imaging apparatus for caries detection according to an alternate embodiment using a polarizing beamsplitter to provide polarized light.
Figure 4A:
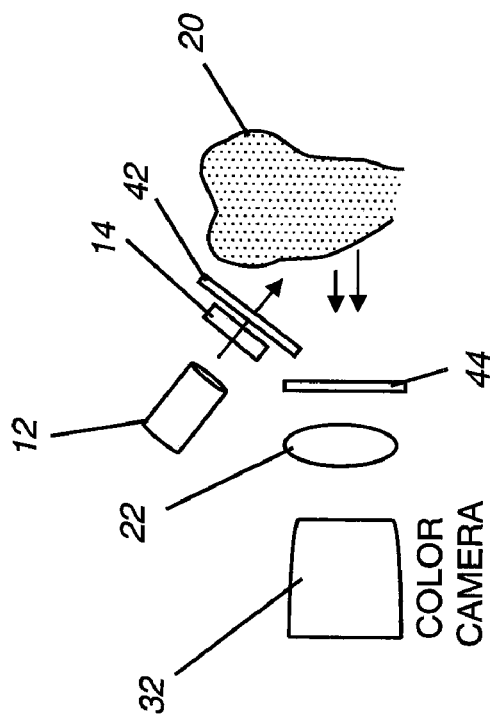
FIG. 4A is a schematic block diagram of an imaging apparatus for caries detection according to an alternate embodiment using polarized light.

Referring to FIG. 4A, there is shown an embodiment of imaging apparatus 10 that employs a polarizer 42 in the path of illumination light. Polarizer 42 passes linearly polarized incident light. An optional analyzer 44 may also be provided in the path of image-bearing light from tooth 20 as a means to minimize the specular reflectance component. With this polarizer 42/analyzer 44 combination as polarizing elements, reflectance light sensed by camera 30 or 32 is predominantly back-scattered light, that portion of the reflectance that is desirable for combination with the fluorescence image data according to the present invention.

An alternate embodiment, shown in FIG. 4B, employs a polarizing beamsplitter 18 (sometimes termed a polarization beamsplitter) as a polarizing element. In this arrangement, polarizing beamsplitter 18 advantageously performs the functions of both the polarizer and the analyzer for image-bearing light, thus offering a more compact solution. Tracing the path of illumination and image-bearing light shows how polarizing beamsplitter 18 performs this function. Illumination from light source 12 is essentially unpolarized. Polarization beamsplitter 18 transmits P-polarization, as shown by the dotted arrow in FIG. 4B, and reflects S-polarization, directing this light to tooth 20. At a caries infection site, back-scattering depolarizes this light. Polarizing beamsplitter 18 treats the back-scattered light in the same manner, transmitting the P-polarization and reflecting the S-polarization. The resulting P-polarized light can then be detected at monochrome camera 30 (with suitable filter as was described with reference to FIG. 1) or color camera 32. Because specular reflected light is S-polarized, polarizing beamsplitter 18 effectively removes this specular reflective component from the light that reaches camera 30, 32.

Polarized illumination results in further improvement in image contrast, but at the expense of light level, as can be seen from the description of FIGS. 4A and 4B. Hence, when using polarized light in this way, it may be necessary to employ a higher intensity light source 12. This employment of polarized illumination is particularly advantaged for obtaining the reflectance image data and is also advantaged when obtaining the fluorescence image data, increasing image contrast and minimizing the effects of specular reflection.

One type of polarizer 42 that has particular advantages for use in imaging apparatus 10 is the wire grid polarizer, such as those available from Moxtek Inc. of Orem, Utah and described in U.S. Pat. No. 6,122,103 (Perkins et al.) The wire grid polarizer exhibits good angular and color response, with relatively good transmission over the blue spectral range. Either or both polarizer 42 and analyzer 44 in the configuration of FIG. 4A could be wire grid polarizers. Wire grid polarizing beamsplitters are also available, and can be used in the configuration of FIG. 4B.

The method of the present invention takes advantage of the way the tooth tissue responds to incident light of sufficient intensity, using the combination of fluorescence and light reflectance to indicate carious areas of the tooth with improved accuracy and clarity. In this way, the present invention offers an improvement upon existing non-invasive fluorescence detection techniques for caries. As was described in the background section given above, images that have been obtained using fluorescence only may not clearly show caries due to low contrast. The method of the present invention provides images having improved contrast and is, therefore, of more potential benefit to the diagnostician for identifying caries.

In addition, unlike earlier approaches using fluorescence alone, the method of the present invention also provides images that can be used to detect caries in its very early incipient stages. This added capability, made possible because of the perceptible back-scattering effects for very early carious lesions, extends the usefulness of the fluorescence technique and helps in detecting caries during a reversible phase, so that fillings or other restorative strategies might not be needed.

Interproximal Caries Detection

As was described earlier in the background information, interproximal caries detection presents a more formidable problem for dental imaging than does caries that occurs on tooth surfaces that are more easily visible. In order to take advantage of the contrast enhancement capability of the FIRE technique for caries detection on all surfaces, it is necessary to provide an implementation scheme that takes into consideration factors such as the complex contour of the tooth surface and the accessibility of interproximal areas to incident light, so that high contrast detection can be obtained for caries on all surfaces, including interproximal caries.

Various illumination arrangements for implementing FIRE have been previously discussed, including using single or multiple light sources from normal incidence and from off-axis-angle incidence. These illumination arrangements provide high contrast FIRE detection of buccal/labial, lingual, and occlusal caries, but not all of them work well for interproximal caries. Interproximal caries is not as accessible to light at normal incidence as light from an appropriate off-axis angle. More specifically, from the perspective of the camera, lesion on the right interproximal surface is better accessed by light directed from the right side of the camera, and lesion on the left interproximal surface is better accessed by light directed from the left side of the camera. However, the site of interproximal caries is not known a priori. To provide the best solution for interproximal caries detection using FIRE, conventional wisdom might suggest illuminating with more than one light source from more than one angle. But in actuality, such multiple angle illumination produces sub-optimal FIRE results. FIGS. 11 to 13 illustrate how the contrast of FIRE detection is sensitive to the illumination arrangement.

Figure 12B:
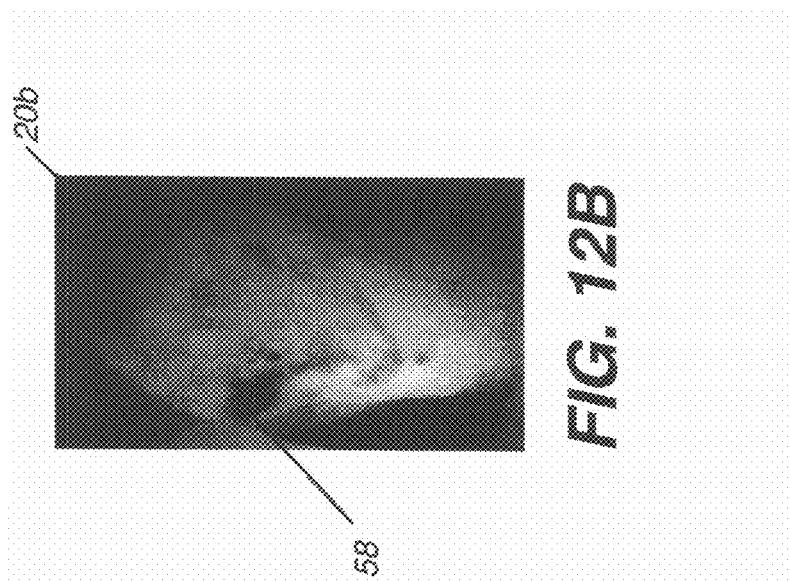
FIGS. 12A and 12B illustrate angled illumination from another side of the camera and the resulting FIRE image.
Figure 12A:
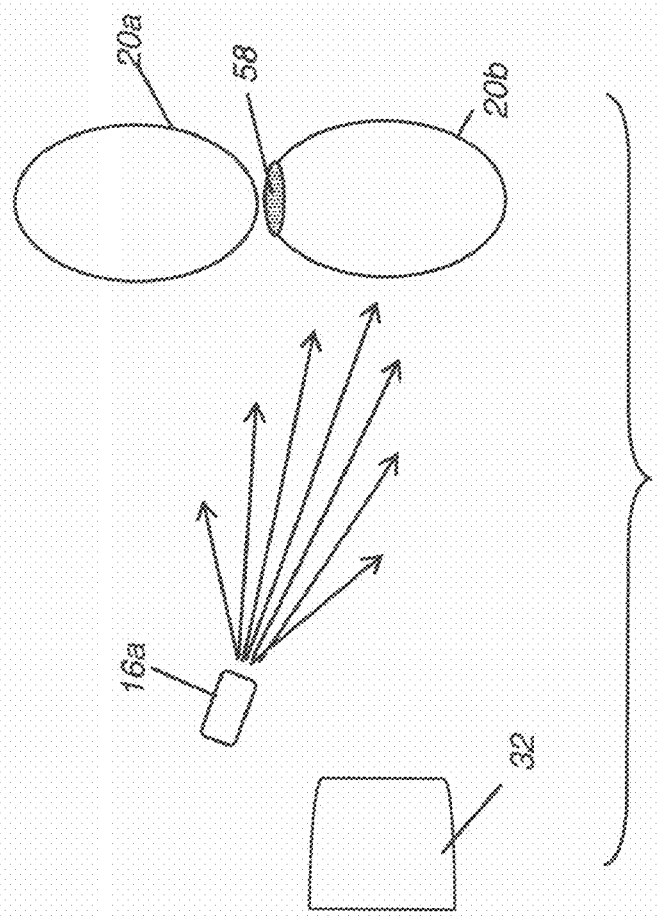
Figure 13B:
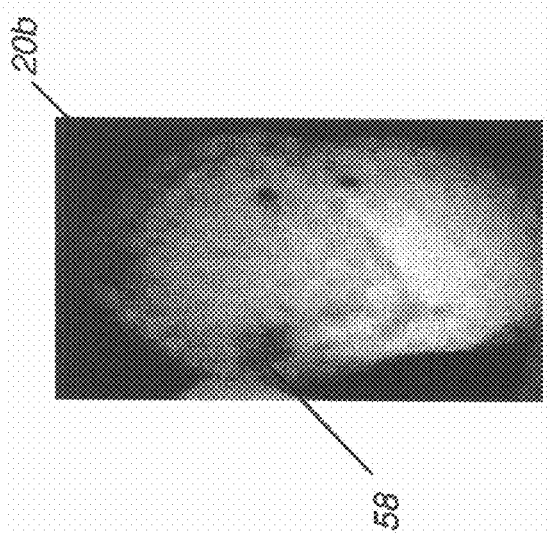
FIGS. 13A and 13B illustrate angled illumination from both sides of the camera and the resulting FIRE image.
Figure 13A:
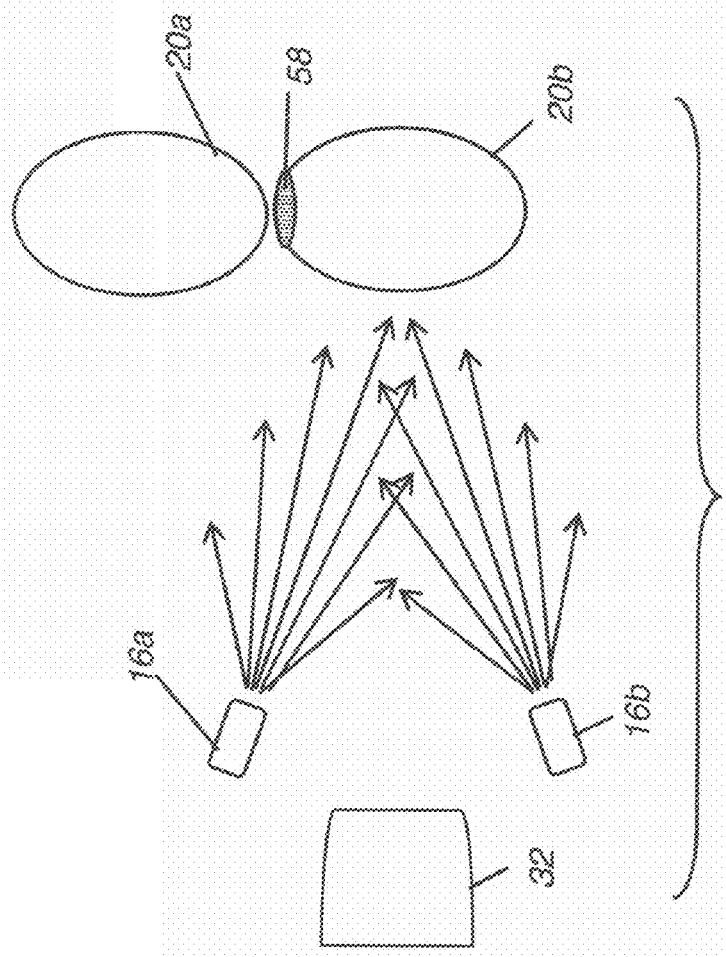

FIGS. 11A, 11B, 12A, 12B, 13A, and 13B show by example the use of varying illumination angles on tooth 20b with interproximal carious region 58 and the results that can be obtained. FIGS. 11A, 12A, and 13A are top views showing light sources 16a and 16b directing light toward tooth 20b at various angular arrangements. FIGS. 11B, 12B, and 13B show the corresponding results, using FIRE imaging, for illumination provided at each of these angular arrangements. Referring first to FIG. 11A, a light source 16b directs illumination from a side of camera 32 opposite to the side of tooth 20b where interproximal carious region 58 is; this angularly directed light relatively poorly illuminates interproximal carious region 58. The resulting FIRE image shown in FIG. 11B does not show much contrast enhancement, as a result of light scattered and reflected from adjacent tooth 20a. This scattered light creates unwanted background light that effectively "washes out" the contrast enhancement that could otherwise be obtainable with FIRE.

Turning next to FIG. 12A, there is shown an arrangement with illumination at a more favorable angle, that is, from a light source 16a directed from a side of camera 32 that is on the same side of tooth 20b where interproximal carious region 58 is. Less of the illumination is scattered from adjacent tooth 20a, so that the contrast enhancement in the FIRE image, as shown in FIG. 12B, is retained. With the higher contrast FIRE image, interproximal carious region 58 is more distinctly visible and thus better detected.

FIGS. 13A and 13B show the case where tooth 12b is simultaneously illuminated by both light sources 16a and 16b. While such a scheme increases the overall illumination light level, the resulting FIRE image contrast enhancement, as shown in FIG. 13B, is actually less than that achieved when only light source 16a is used. By also illuminating with light source 16b, the potential contrast enhancement is lost for the same reason as illustrated in FIGS. 11A and 11B.

As the examples of FIGS. 11A through 13B show, interproximal caries imaging benefits from the contrast enhancement of FIRE only with light directed from one side—the same side of the affected tooth as the caries condition. More precisely, relative to a normal to the affected interproximal surface, illumination from an acute angle provides a FIRE image that exhibits better contrast enhancement than does illumination from an obtuse angle. And the amount of contrast enhancement using FIRE is actually less when simultaneous illumination from multiple angles are used, as was demonstrated in the example of FIGS. 13A and 13B.

Of course, the location of carious region 58 is not known in advance. To ensure that interproximal caries located on either side of the tooth is detected with high contrast, angled illumination must be provided from both sides of the camera, but at different times.

Therefore, to implement the FIRE method for contrast-enhanced detection of caries on all surfaces, including interproximal caries, the method of the present invention obtains multiple FIRE images at a given camera location, modulating the illumination characteristics by varying the illumination angle for each image. While buccal/labial or lingual caries will be imaged with contrast enhancement that is not so sensitive to the illumination angle, interproximal caries will show up in the FIRE images having different amounts of contrast enhancement, ranging from poor to optimal, with the illumination angle. The important point is that the set of FIRE images will contain one image that captures the interproximal caries with the optimal contrast enhancement. The set of FIRE images generated from the captured fluorescence and reflectance images can all be displayed for visual analysis by the diagnostician. In the preferred embodiment, they can be processed by processing apparatus 38 (FIGS. 1, 2) to select and display only the optimal contrast FIRE image for the diagnostician to make diagnosis of caries conditions.

Referring to FIGS. 8A and 8B there is shown, in perspective view, a carious region 58 between teeth 20a and 20b that is imaged using illumination from two different directions at different times. Color camera 32 is held stationary in position directly facing tooth 20b. A first set of fluorescence image and reflectance image are captured when light source 16a singly illuminates tooth 20b from a first angle, to the left in the view of FIG. 8A. This first set of fluorescence image and reflectance image will be combined to generate a first FIRE image. Then a second set of fluorescence image and reflectance image are captured when only light source 16b is energized, providing illumination at an opposite angle, as shown in FIG. 8B. A second FIRE image is obtained from this second set of captured fluorescence and reflectance images.

Figure 16:
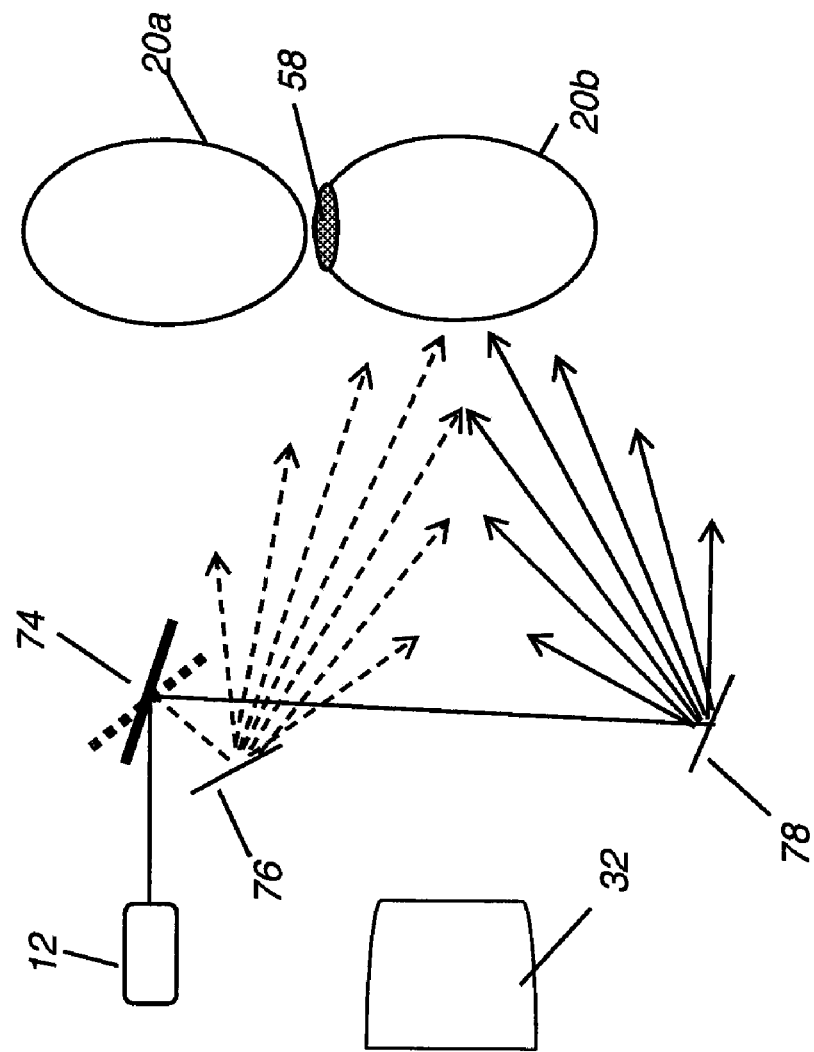
FIG. 16 shows an alternate embodiment in which only one light source is used to provide the illumination light from both angles, utilizing a movable mirror.

In an alternate embodiment, as shown in FIG. 16, only one light source 12 is used to provide the illumination light from both angles. In this case, a movable mirror 74 directs light to mirror 76 when illuminating from one angle (light rays represented by dotted lines), and then directs light to mirror 78 when illuminating from the other angle (light rays represented by solid lines). Movable mirror 74 can be implemented by a mirror mounted on a rotating galvanometer or a translating slide, for example.

Figure 9:
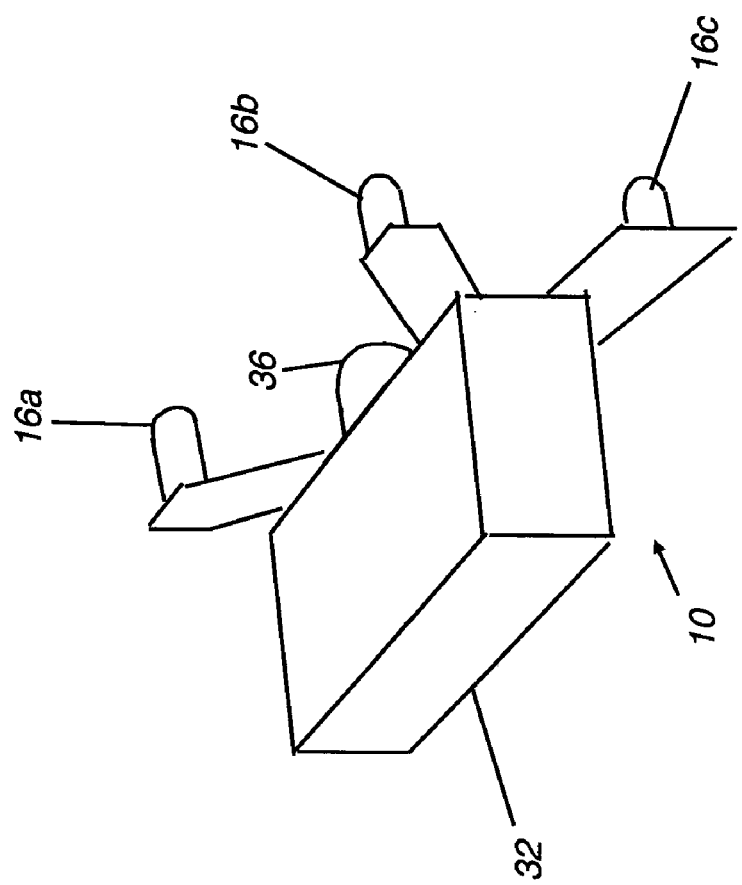
FIG. 9 is a perspective view of a camera arrangement for providing illumination from different angles.
Figure 10:
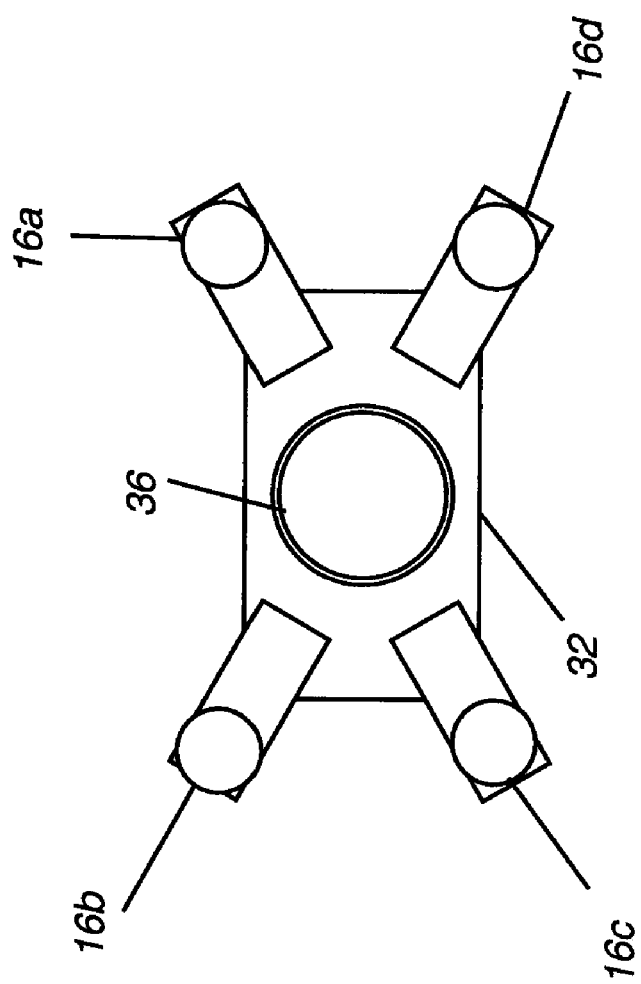
FIG. 10 is a plan view of the front of a camera such as that shown in FIG. 9.

FIGS. 9 and 10 show perspective and plan views, respectively, of one embodiment of imaging apparatus 10 having camera 32 outfitted with multiple light sources 16a, 16b, 16c, and 16d (not shown in figure), arranged at different positions relative to a camera lens 36. Light sources 16a, 16b, 16c, and 16d could be attached as an integral part of color camera 32 as shown, or could be on a separate apparatus. In one embodiment, four sets of fluorescence and reflectance images for constructing four FIRE images are obtained, each set using each light source 16a, 16b, 16c, and 16d, energized singly. Optionally, combinations of light sources 16a, 16b, 16c, and 16d could also be employed. For example, a FIRE image is generated from a set of fluorescence and reflectance images captured illuminating only from one side by energizing light sources 16b and 16c simultaneously; then another FIRE image is generated from another set of fluorescence and reflectance images captured illuminating only from the other side by energizing light sources 16a and 16d simultaneously. By obtaining a sequence of FIRE images in this manner, varying only the illumination angle and keeping color camera 32 stationary, one of the FIRE images captures any interproximal lesion present with the optimal contrast enhancement, thus improving the diagnostic capabilities. In this way, the present invention provides an improved technique that takes advantage of the contrast enhancement capability of the FIRE technique for caries detection on all surfaces In one embodiment, each light source 16a, 16b, 16c, 16d is an LED, provided with suitable optics for directing light toward a tooth at a suitable angle. An adjustable mounting is optionally provided, so that one or more of light sources 16a, 16b, 16c, 16d can be appropriately oriented for imaging. Alternatively, clusters having two or more light-emitting elements may be used for one or more of light sources 16a, 16b, 16c, or 16d. Other types of illuminating elements may be employed, such as lasers, lamps, or light sources directed to tooth 20 using optical fibers or other types of light guides.

Light sources 16a, 16b, 16c, 16d could emit light over the same wavelength band or could provide light at different wavelengths. In the preferred embodiment, all light sources 16a, 16b, 16c, and 16d emit light at the same wavelength. In an alternate embodiment, light sources 16a and 16b provide light of appropriate energy level and wavelength for exciting fluorescent emission. Light sources 16c and 16d provide light at wavelength and energy levels best suited for back-scattered reflectance imaging. As with other embodiments, numerous possible imaging sequences can be used, with numerous possible combinations of light sources 16a, 16b, 16c, 16d used singly or simultaneously. In the preferred embodiment, the fluorescence image is obtained only once, with light from a single illumination angle or all illumination angles; then, reflectance image is obtained using light from more than one illumination angle. In this case, the same fluorescence image is combined with each reflectance image to generate a distinct FIRE image for each illumination angle. Alternately, a fluorescence image and a reflectance image can be captured for each illumination angle. As yet another alternative, one light source could provide white light illumination.

Workflow

Figure 14:
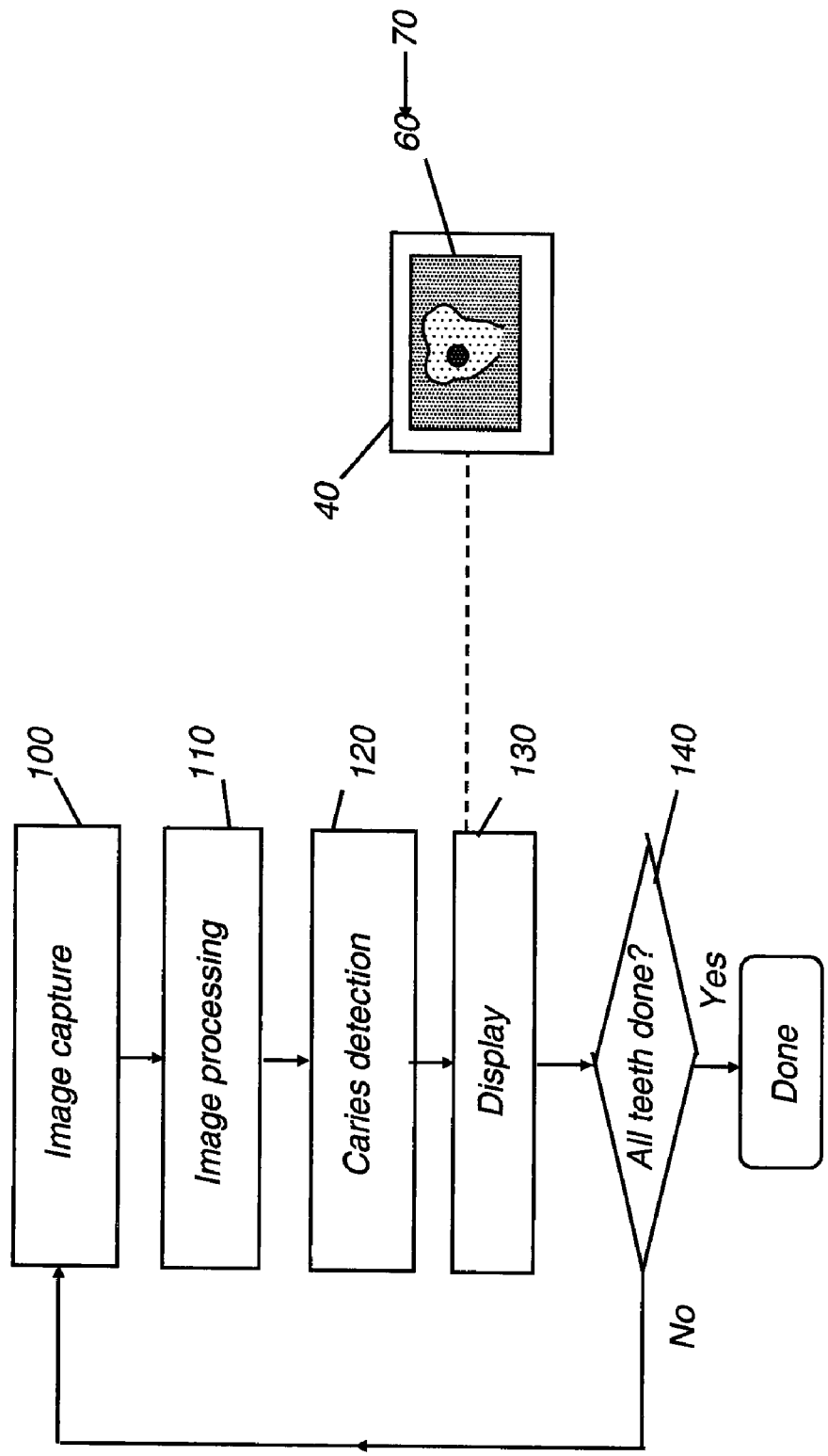
FIG. 14 is a flow chart of the work flow for caries detection using the method of the present invention.

Imaging apparatus 10 allows imaging of each tooth by a dental practitioner and automatic processing of each image, with displayed results for viewing and diagnostic assessment. FIG. 14 shows the sequence of steps for imaging workflow in one embodiment using a highly automated sequence. In an image capture step 100, the dentist or technician positions color camera 32 and its illumination apparatus at a tooth surface. The dental practitioner then instructs imaging apparatus 10 to obtain the image, such as by pressing a control button or depressing a foot pedal. Color camera 32 takes the sequence of images at this position. The image capture sequence consists of energizing the light source from a first side and capturing the fluorescence and reflectance images, then energizing the light source from a second side and capturing the fluorescence and reflectance images. Optionally, a white light image can also be captured. Then, in an image processing step 110, processing apparatus 38 executes image processing to generate a first FIRE image from fluorescence and reflectance images captured with illumination from the first side and a second FIRE image from fluorescence and reflectance images captured with illumination from the second side. Processing apparatus 38 then runs algorithms that compares the image contrast of the two FIRE images and select the one with the best contrast. A caries detection step 120 can then be executed, using image analysis algorithms on the selected best-contrast FIRE image 70 to detect suspected carious areas and, optionally, to assess the severity of the lesions in some manner. A display step 130 follows, in which the selected best-contrast FIRE image 70 is presented on display 40. The suspected carious areas may or may not be marked or highlighted in the selected FIRE image 70 on display. The fluorescence images, reflectance images, the FIRE images generated for both illumination configurations, the selected FIRE image 70, and white light image associated with the particular face of the tooth are all stored in a data base; they can be retrieved to be displayed for further examination. A loop logic step 140 then executes, causing steps 100, 110, 120, and 130 to be executed for each tooth surface of interest. If all teeth are to be screened, steps 100, 110, 120, and 130 are executed for the buccal/labial, lingual, and occlusal surfaces of each tooth. Image capture step 100 can be repeated in cases where the dental practitioner desires a different image.

Figure 15:
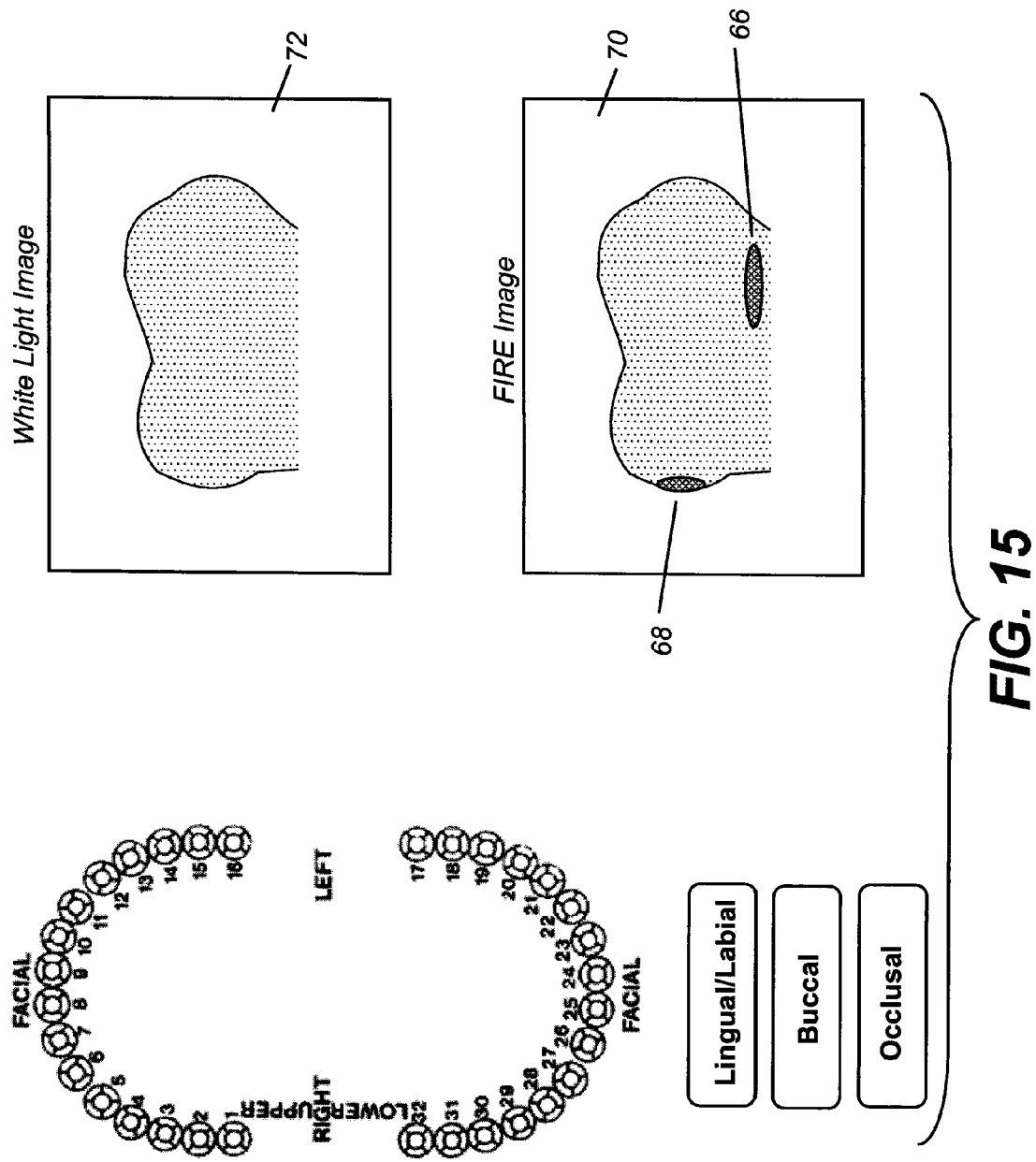
FIG. 15 shows a display interface for dental practitioner to make caries diagnosis.

At the completion of the image capture for all the teeth of a patient, display 40 interface may have the appearance shown in FIG. 15. Referring to FIG. 15, clicking on a particular tooth on the dental chart and selecting a particular tooth surface button retrieves the associated set of images. By way of example, the white light image 72 may be displayed along side of the selected FIRE image 70, the latter showing both buccal caries 66 and interproximal caries 68 at high contrast. If desired, the diagnostician may choose to display the reflectance and/or fluorescence images also. The diagnostician makes diagnosis of the tooth condition based on these images.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. Thus, what is provided is an apparatus and method for improved contrast detection of caries on all surfaces, including interproximal surface, using combined effects of back-scattered reflectance and fluorescence.

PARTS LIST

10 imaging apparatus
12 light source
13 diffuser
14 lens
16a light source
16b light source
16c light source
16d light source
18 polarizing beamsplitter
20 tooth
20a tooth
20b tooth
22 lens
26 filter
28 filter
30 monochrome camera
32 color camera
34 beamsplitter
36 lens
38 processing apparatus
40 display
42 polarizer
44 analyzer
50 fluorescence image
52 reflectance image
54 white-light image
58 carious region
60 FIRE image
62 threshold image
64 enhanced threshold FIRE image
66 buccal caries
68 interproximal caries
70 selected FIRE image
72 white light image
74 movable mirror
76 mirror
78 mirror
100 image capture step
110 image processing and analysis step
120 caries detection step
130 display step
140 loop logic step

The invention claimed is:

1. A method for caries detection comprising:
   (a) disposing an image capture device at a position facing a tooth;
   (b) obtaining fluorescence image data from the tooth by illuminating the tooth to excite fluorescent emission and obtaining a fluorescence image from the emitted light;
   (c) obtaining a first enhanced image of the tooth by:
       (i) illuminating the tooth at a first incident angle;
       (ii) obtaining, from back-scattered light, back-scattered reflectance image data from the tooth tissue; and
       (iii) combining the back-scattered reflectance image data with the fluorescence image data to form the first enhanced image;
   (d) obtaining a second enhanced image of the tooth by:
       (i) illuminating the tooth at a second incident angle, different from the first incident angle;
       (ii) obtaining, from back-scattered light, back-scattered reflectance image data from the tooth tissue; and
       (iii) combining the back-scattered reflectance image data with the fluorescence image data to form the second enhanced image;
   (e) analyzing the first and second enhanced images to select a best-contrast image; and
   (f) displaying the best-contrast image.

2. The method of claim 1 wherein step (b) is performed using the same illumination as in step (c).

3. The method of claim 1 wherein step (b) is performed using the same illumination as in step (d).

4. The method of claim 1 wherein step (b) is performed using both the illuminations in steps (c) and (d).

5. The method of claim 1 wherein the caries is interproximal.

6. The method of claim 1 wherein the image capture device is a camera.

7. The method of claim 6 wherein the camera is handheld.

8. The method of claim 1 wherein the illumination in step (b) is performed using light of a first wavelength, and the illumination in steps (c) and (d) are performed using light of a second, different wavelength.

9. The method of claim 1 wherein the illumination in steps (b), (c), and (d) are performed using light of the same wavelength.

10. The method of claim 1 wherein the incident light includes wavelengths between about 300 and 500 nm.

11. The method of claim 1 wherein obtaining the fluorescence image data comprises the step of using a green filter.

12. The method of claim 1 wherein obtaining the back-scattered reflectance image data comprises the step of using a blue filter.

13. The method of claim 1 wherein the image capture device is a color camera.

14. The method of claim 1 wherein the fluorescence image data and back-scattered image data are obtained from different color planes of a single, full-color image capture.

15. The method of claim 1 wherein the image capture device is a monochrome camera and wherein the step of obtaining back-scattered reflectance image data further comprises providing at least one spectral filter.

16. The method of claim 1 wherein the step of combining fluorescence and back-scattered reflectance image data comprises applying an image processing algorithm.

17. The method of claim 1 wherein the step of combining comprises, for at least one pixel:
   (a) multiplying the fluorescence image data value by a first coefficient to form a first value;
   (b) multiplying the reflectance image data value by a second coefficient to form a second value; and
   (c) obtaining the difference between the first and second values.

18. The method of claim 17 wherein the second coefficient is one.

19. The method of claim 1 wherein illuminating the tooth comprises energizing at least two light sources.

20. The method of claim 19 wherein the at least two light sources are energized over different time intervals.

21. The method of claim 1 wherein illuminating the tooth comprises energizing a single light source.

22. The method of claim 1 further comprising:
   a) directing a white light toward the tooth; and
   b) obtaining and displaying a white light image of the tooth.

23. The method of claim 1 further comprising providing a polarizer in the path of incident light to the tooth.

24. The method of claim 1 further comprising providing an analyzer in the path of light received from the tooth.

25. The method of claim 1 wherein the step of illuminating the tooth further comprises the step of providing a beamsplitter in the path of the incident light.

26. The method of claim 1 wherein the step of illuminating the tooth further comprises the step of providing a polarization beamsplitter in the path of the incident light.

27. The method of claim 26 wherein the polarization beamsplitter is a wire grid beamsplitter.

28. The method of claim 1 wherein the step of illuminating the tooth comprises the step of energizing a laser.

29. The method of claim 1 wherein the step of illuminating the tooth comprises the step of energizing an LED.

30. The method of claim 1 wherein the step of illuminating the tooth comprises the step of energizing a lamp.

31. The method of claim 1 wherein the step of illuminating the tooth further comprises directing light through a light guiding structure.

32. The method of claim 1 wherein the step of illuminating the tooth further comprises directing light through a diffuser.

33. The method of claim 1 wherein the step of obtaining fluorescence image data comprises the step of providing a telecentric optical element in the path of image-bearing light.

34. A system for detecting dental caries on a tooth comprising:
   (a) a first incident light directed toward the tooth from a first incident angle, wherein the first incident light generates backscattered light from the tooth, forming a first backscattered reflectance image;
   (b) a second incident light directed toward the tooth from a second incident angle, wherein the second incident light generates backscattered light from the tooth, forming a second backscattered reflectance image;
   (c) a third incident light directed toward the tooth, wherein the third incident light generates a fluorescent response from the tooth, forming a fluorescence image;
   (d) an image capture device disposed at a position facing the tooth for capturing the first backscattered reflectance image, the second backscattered reflectance image, and the fluorescence image;
   (e) an image processor for processing image data obtained from the image capture device to combine the first backscattered reflectance image and the fluorescence image to generate a first enhanced image, to combine the second backscattered reflectance image and the fluorescence image to generate a second enhanced image, and further to analyze the first and second enhanced images to select a best-contrast image; and
   (f) a display for displaying the best-contrast image.

35. The system of claim 34 wherein the third incident light is the same as the first incident light.

36. The system of claim 34 wherein the third incident light is the same as the second incident light.

37. The system of claim 34 wherein the third incident light is the first and second incident lights combined.

38. The system of claim 34 wherein the first incident light and the second incident light come from the same light source.

39. The system of claim 34 wherein the first and second incident lights are of one wavelength, and the third incident light is of a second, different wavelength.

40. The system of claim 34 wherein the first, second, and third incident lights are of the same wavelength.

* * * * *